United States Patent [19]

Ikezaki et al.

[11] 4,218,479
[45] Aug. 19, 1980

[54] NOVEL BENZYLALCOHOLS AND PHARMACEUTICAL COMPOSITIONS AND USE THEREOF

[75] Inventors: Muneyoshi Ikezaki, Ageo; Hisao Otsuka, Omiya; Hajime Iwai, Hasuda; Masanori Inamasu, Misato; Takashi Morita, Kawagoe, all of Japan

[73] Assignee: Tanabe Seiyaku Co., Ltd., Osaka, Japan

[21] Appl. No.: 906,965

[22] Filed: May 18, 1978

[30] Foreign Application Priority Data

Jun. 2, 1977 [JP] Japan .................................. 52-65405

[51] Int. Cl.$^2$ .................... A61K 31/135; C07C 91/16; C07C 91/22; C07C 91/34
[52] U.S. Cl. .................................. 424/330; 260/570.6
[58] Field of Search ...................... 424/330; 260/570.6

[56] References Cited

U.S. PATENT DOCUMENTS

| | | | |
|---|---|---|---|
| 3,869,474 | 3/1975 | Miura et al. | 260/570.6 |
| 3,952,021 | 4/1976 | Ikezaki et al. | 424/330 |
| 4,032,575 | 6/1977 | Ikezaki et al. | 424/330 |
| 4,072,759 | 2/1978 | Ikezaki et al. | 424/330 |
| 4,131,686 | 12/1978 | Ikezaki et al. | 424/330 |

FOREIGN PATENT DOCUMENTS

| | | | |
|---|---|---|---|
| 85409 | 10/1975 | Australia | 260/570.6 |
| 1163814 | 10/1958 | France | 260/570.6 |
| 2405660 | 10/1974 | Netherlands | 424/330 |

*Primary Examiner*—Douglas W. Robinson
*Attorney, Agent, or Firm*—Bierman & Bierman

[57] ABSTRACT

Racemic or optically active α-(2,3,4-trimethoxyphenethylaminomethyl)-2-hydroxybenzylalcohol [I] may be prepared by condensing 2,3,4-trimethoxyphenethylamine with 2-benzyloxyphenylglyoxal or its hydrate, reducing the resultant α(2,3,4-tri-methoxyphenethylimino)-2-benzyloxyacetophenone to give α(2,3,4-trimethoxyphenethylaminomethyl)-2-benzyloxybenzylalcohol, if required, resolving the 2-benzyloxybenzylalcohol derivative into each of its optically active enantiomers, and subjecting the racemic modification or optically active enantiomer of said 2-benzyloxybenzylalcohol derivative to catalytic hydrogenation. The compound [I] and pharmaceutically acceptable acid addition salts thereof are useful as anti-diabetic agents. They may be also used in the treatment of thrombosis.

6 Claims, No Drawings

NOVEL BENZYLALCOHOLS AND PHARMACEUTICAL COMPOSITIONS AND USE THEREOF

This invention relates to a novel benzylalcohol derivative and a process for preparing the same. More particularly, it relates to racemic or optically active α-(2,3,4-trimethoxyphenethylaminomethyl)-2-hydroxybenzylalcohol of the formula:

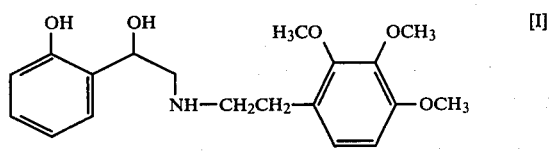

and pharmaceutically acceptable acid addition salts thereof.

It is known that α-(3,4,5-trimethoxyphenethylaminomethyl)-3,4-dihydroxybenzylalcohol and α-(3,4-dimethoxyphenethylaminomethyl)-3,4-dihydroxybenzylalcohol are prepared by hydrogenating the corresponding 3,4-dibenzyloxybenzylalcohol or 3,4-dibenzyloxyacetophenone derivative in the presence of palladium-carbon (U.S. Pat. Nos. 3,869,474 and 3,952,021). These compounds show selective activation of adrenergic $\beta_1$-receptor and are useful as cardiotonic agents. It is also known that α-(3,4-dimethoxyphenethylaminomethyl)-2-hydroxybenzylalcohol shows a blood sugar-lowering activity and can be used as an anti-diabetic agent (Japanese patent application No. 127,789/1975 which was laid open to the public under No. 51,333/1977).

We have now found that the benzylalcohol derivative [I] can induce a remarkable decrease of blood sugar and is useful as an anti-diabetic agent. The blood sugar-lowering activity of the benzylalcohol derivative [I] is about 10 times stronger than that of Phenformin (Chemical name: 1-phenethyl-biguanide). For example, when dl-α-(2,3,4-trimethoxyphenethylaminomethyl)-2-hydroxybenzylalcohol ½ oxalate (Dose: 10 mg/kg) is administered orally to mice immediately before subcutaneous injection of glucose (one g/kg), the increased blood sugar level is about 50% lower than that of a group of mice having injected glucose only. On the other hand, when examined under the same condition as above, 100 mg/kg of Phenformin are required to obtain almost the same blood sugar-lowering activity as in case of oral administration of said benzylalcohol derivative (Dose: 10 mg/kg). The benzylalcohol derivative of the invention can also decrease aggregation of blood platelets and may be used in the treatment of thrombosis, while α-(3,4-dimethoxyphenethylaminomethyl)-2-hydroxybenzylalcohol disclosed in Japanese patent application No. 127,789/1975 shows no substantial effect upon alleviation of said thrombosis. For example, when dl-α-(2,3,4-trimethoxyphenethylaminomethyl)-2-hydroxybenzylalcohol hydrochloride of the invention is administered orally to rats at the dose of 100 mg/kg, said benzylalcohol derivative can prevent the aggregation of blood platelets in the plasma by about 23%. Further, the benzylalcohol derivative [I] shows no substantial adrenergic β-action, such as cardiac contractile action (one of the side effects of an anti-diabetic agent), and the acute toxicity thereof is also considerably low. For example, the maximum tolerance dose (M.T.D.) of dl-α-(2,3,4-trimethoxyphenethylaminomethyl)-2-hydroxybenzylalcohol ½ oxalate, which is estimated 48 hours after intraperitoneal injection thereof to a group of four mice, is more than 300 mg/kg.

The benzylalcohol derivative [I] of the present invention can be used for pharmaceutical use either in the form of a racemic modification or in an optically active form. The benzylalcohol derivative [I] can also be used for pharmaceutical use as the free base or a salt thereof. The base and salt thereof are readily convertible from one to the other by conventional methods. Examples of the pharmaceutically acceptable acid addition salts include inorganic acid addition salts such as hydrochloride, phosphate, nitrate and sulfate, and organic acid addition salts such as acetate, lactate, tartarate, fumarate, maleate, oxalate, succinate, methanesulfonate and benzoate. The benzylalcohol derivative [I] may be administered either orally or parenterally, and may be further used in conjunction or admixture with a pharmaceutical excipient which is suitable for oral or parenteral administration. When administered for inducing the decrease of blood sugar, a suitable daily dose for oral administration of the benzylalcohol derivative [I] may be 5 μg to 10 mg, especially 20 μg to 2 mg, per kg of body weight. On the other hand, when administered for decreasing the aggregation of blood platelets, a suitable daily dose for oral administration of the benzylalcohol derivative [I] may be 500 μg to 200 mg, especially one mg to 100 mg, per kg of body weight.

According to the present invention, the benzylalcohol derivative [I] can be prepared by the steps of:

(i) condensing 2,3,4-trimethoxyphenethylamine with a phenylglyoxal derivative of the formula:

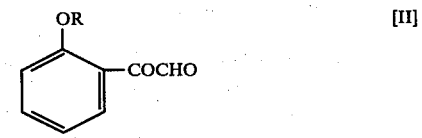

wherein R is benzyl; or a hydrate thereof to give an α-(2,3,4-trimethoxyphenethylimino)acetophenone derivative of the formula:

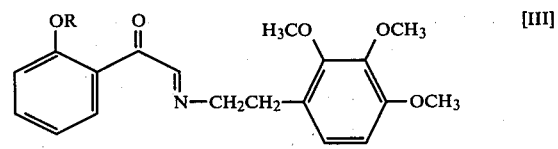

wherein R is the same as defined above, (ii) reducing the acetophenone derivative [III] to give α-(2,3,4-trimethoxyphenethylaminomethyl)-2-benzyloxybenzylalcohol of the formula:

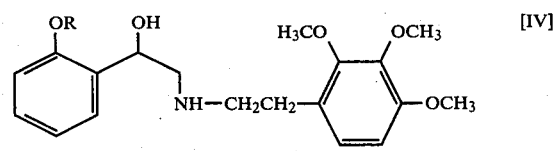

wherein R is the same as defined above, (iii) if required, resolving the 2-benzyloxybenzylalcohol derivative [IV] into each of its optically active enantiomers, and (iv) subjecting the racemic modification or optically active enantiomer of said 2-benzyloxybenzylalcohol derivative [IV] to catalytic hydrogenation.

The starting compound [II] is readily obtained. For example, the compound [II] is obtained by oxidation of 2-benzylacetophenone with selenium dioxide according to a method known per se [e.g., Chemical Abstracts, Vol. 66, 46399c(1967); ibid. Vol. 72, 89963y(1970)].

The condensation of 2,3,4-trimethoxyphenethylamine with the phenylglyoxal derivative [II] or a hydrate thereof can be readily accomplished. For example, the compound [III] is prepared by admixing said starting compounds in the presence or absence of a catalyst in a solvent. It is preferred to carry out the reaction at a temperature of 0° to 50° C. Preferred examples of the reaction solvent include dimethylsulfoxide and lower alkanols (e.g., methanol, ethanol). p-Toluenesulfonic acid is suitable as the catalyst. The α-(2,3,4-trimethoxyphenethylimino)acetophenone derivative [III] thus obtained may be used in the subsequent reaction without isolating it from the reaction solution.

The 2-benzyloxybenzylalcohol derivative [IV] is prepared by treating the compound [III] with a reducing agent in a solvent. Suitable examples of the reducing agent include an alkali metal borohydride (e.g., sodium borohydride, potassium borohydride, lithium borohydride), lithium aluminium hydride, diboran and aluminium hydride. Lower alkanols (e.g., methanol, ethanol, propanol), a mixture of said lower alkanol and water, tetrahydrofuran, dioxane and the like are suitable as the reaction solvent. It is preferred to carry out the reaction at a temperature of −10° to 50° C.

The 2-benzyloxybenzylalcohol derivative [IV] thus obtained always exists in the form of a racemic modification and may be, if required, resolved into each of its optically active enantiomers. The optical resolution of the 2-benzyloxybenzylalcohol derivative [IV] may be carried out by reacting the racemic modification with a resolving agent in a solvent to form the diastereoisomeric salts thereof, and separating said diastereoisomers into the components thereof by selective recrystallization. By said selective recrystallization, the least soluble diastereoisomer is recovered as crystals from the reaction mixture and the more soluble diastereoisomer remains soluble therein. It is preferred to carry out the selective recrystallization at a temperature of −20° to 25° C. Derivatives of optically active tartaric acid (e.g., optically active enantiomers of dibenzoyltartaric acid, diacetyltartaric acid and monobenzoyltartaric acid), d-camphorsulfonic acid, d-α-bromocamphorsulfonic acid, L-(−)-malic acid, l-mandelic acid, quinic acid and optically active amino acid or their derivatives (e.g., optically active enantiomers of N-acetylphenylalanine, glutamic acid and N-carbobenzyloxyglutamic acid) may be used as the resolving agent. The solvent which is employed in this resolution procedure should be the one in which the solubilities of the two diastereoisomers are sufficiently different from each other to permit separation. For this purpose it is suitable to use water, lower alkanols (e.g., methanol, ethanol), ethylacetate, chloroform, dimethylformamide or a mixture of these solvents.

The catalytic hydrogenation of the racemic 2-benzyloxybenzylalcohol derivative [IV] or its optically active enantiomers is carried out in the presence of a catalyst in a solvent and in a hydrogen atmosphere. Preferred examples of the catalysts include platinum, platinum dioxide, palladium-black, palladium-carbon and the like. Lower alkanols (e.g., methanol, ethanol) are preferably employed as the solvent. It is preferred to carry out the reaction at a temperature of 20° to 50° C. under one to 5 atmospheres pressure.

Practical and presently-preferred embodiments of the present invention are illustratively shown in the following Examples.

EXAMPLE 1

(1) 10 g of 2-benzyloxyacetophenone are dissolved in 40 ml of dioxane, and a solution of 6.4 g of selenium dioxide in 3 ml of water is added thereto. The mixture is refluxed for 12 hours. After the reaction is completed, insoluble materials are removed by filtration, and the filtrate is condensed. The residue thus obtained is dissolved in ethyl acetate. The ethyl acetate solution is washed with water, an aqueous sodium bicarbonate solution and water, successively. Then, said solution is dried and evaporated to remove solvent. 10.5 g of 2-benzyloxyphenylglyoxal hydrate are obtained as a crude oil.

(2) 10.5 g of 2-benzyloxyphenylglyoxal hydrate (crude oil) are dissolved in 30 ml of dimethylsulfoxide, and 9 g of 2,3,4-trimethoxyphenethylamine are added thereto. The mixture is stirred at room temperature for 30 minutes, whereby a solution of α-(2,3,4-trimethoxyphenethylimino)-2-benzyloxyacetophenone in dimethylsulfoxide is obtained.

(3) 60 ml of ethanol are added to the α-(2,3,4-trimethoxyphenethylimino)-2-benzyloxyacetophenone solution obtained in paragraph (2). After ice-cooling, 2.5 g of sodium borohydride are added gradually to the solution, and the mixture is stirred at room temperature for 2 hours. The reaction mixture is evaporated to remove ethanol. The residue thus obtained is dissolved in ethyl acetate. The ethyl acetate solution is washed with water, dried and evaporated to remove solvent. The residue is dissolved in ethanol. The ethanol solution is acidified with ethanolic hydrogen chloride and evaporated to remove solvent. The resultant residue is recrystallized from a mixture of ethanol and ether. 13.1 g of α-(2,3,4-trimethoxyphenethylaminomethyl)-2-benzyloxybenzylalcohol hydrochloride are obtained. M.p. 129°–130° C. Yield: 66% (based on 2-benzyloxyacetophenone used)

(4) A mixture of 5 g of α-(2,3,4-trimethoxyphenethylaminomethyl)-2-benzyloxybenzylalcohol hydrochloride, one g of 10% palladium-carbon and 50 ml of 90% aqueous methanol is shaken at room temperature in hydrogen gas atmosphere under atmospheric pressure. After hydrogen uptake is completed, insoluble materials are removed by filtration, and the filtrate is condensed. The residue thus obtained is recrystallized from a mixture of ethanol and ether. 3.4 g of α-(2,3,4-trimethoxyphenethylaminomethyl)-2-hydroxybenzylalcohol hydrochloride are obtained. M.p. 133°–134° C. Yield: 85%

Analysis calculated for $C_{19}H_{25}O_5N\cdot HCl$. C, 59.45; H, 6.83; N, 3.65; Cl, 9.24. Found: C, 59.29; H, 6.82; N, 3.94; Cl, 9.55.

½ oxalate:

M.p. 192° C. (decomp.) (recrystallized from ethanol)

½ succinate:

M.p. 157°–158° C. (recrystallized from 80% aqueous ethanol)

EXAMPLE 2

(1) 6.8 g of α-(2,3,4-trimethoxyphenethylaminomethyl)-2-benzyloxybenzylalcohol hydrochloride are neutralized with 10% aqueous potassium carbonate, and the free base obtained and 3 g of N-acetyl-L-phenylalanine are dissolved in 15 ml of ethyl acetate. 10 ml of ether are added to the ethyl acetate solution, and the mixture is allowed to stand at room temperature for 96 hours. The crystalline precipitates are collected by filtration and recrystallized from a mixture of ethyl acetate and ether. 2.3 g of l-α-(2,3,4-trimethoxyphenethylaminomethyl)-2-benzyloxybenzylalcohol N-acetyl-L-phenylalanine salt are obtained. M.p. 109°–110° C. $[\alpha]_D^{22} -15.2°$ (C=1.0, in methanol)

2.3 g of the salt obtained are dissolved in methylene chloride, and the solution is washed with 10% aqueous potassium carbonate. Then, the solution is dried and evaporated to remove solvent. The crystals thus obtained are recrystallized from isopropyl ether, whereby 1.35 g of l-α-(2,3,4-trimethoxyphenethylaminomethyl)-2-benzyloxybenzylalcohol is obtained. M.p. 82°–83° C. $[\alpha]_D^{22} -43.4°$ (C=1.0, in methanol)

Hydrochloride:
  M.p. 142°–144° C. (recrystallized from a mixture of ethanol and ether)
  $[\alpha]_D^{22} -59.1°$ (C=1.0, in methanol)

½ oxalate:
  M.p. 165°–166° C. (recrystallized from ethanol)
  $[\alpha]_D^{22} -56.8°$ (C=0.5, in methanol)

(2) A mixture of 0.2 g of l-α-(2,3,4-trimethoxyphenethylaminomethyl)-2-benzyloxybenzylalcohol ½ oxalate, 60 mg of 10% palladium-carbon and 10 ml of 90% aqueous methanol is treated in the same manner as described in Example 1-(4). The crude crystals thus obtained is recrystallized from 70% aqueous methanol. 110 mg of l-α-(2,3,4-trimethoxyphenethylaminomethyl)-2-hydroxybenzylalcohol ½ oxalate are obtained. M.p. 193°–194° C. (decomp.) $[\alpha]_D^{22} -35.4°$ (C=0.26, in 70% aqueous methanol)

What we claim is:

1. Racemic α-(2,3,4-trimethoxyphenethylaminomethyl)-2-hydroxybenzylalcohol or a pharmaceutically acceptable acid addition salt thereof.

2. The compound of claim 1, wherein said benzylalcohol is an optically active l-enantiomer.

3. A pharmaceutical composition consisting essentially of a therapeutically effective amount of the compound of claim 1 and a pharmaceutically acceptable carrier.

4. A method of lowering blood sugar and decreasing the aggregation of blood platelets comprising administering to a warm blooded animal a therapeutically effective amount of the compound of claim 1.

5. A method according to claim 4 wherein said amount is from about 5 micrograms to 10 milligrams per kilogram of body weight per day.

6. A method according to claim 5 wherein said amount is from about 20 micrograms to 2 milligrams per kilogram of body weight per day.

* * * * *